(12) United States Patent
Jakkula et al.

(10) Patent No.: US 8,188,751 B2
(45) Date of Patent: May 29, 2012

(54) METHOD AND MEASURING INSTRUMENT FOR MEASURING WATER CONTENT

(75) Inventors: Pekka Jakkula, Oulu (FI); Jarmo Karhu, Oulu (FI); Kari Luostarinen, Jyvaskyla (FI); Matti Limingoja, Oulu (FI)

(73) Assignees: Senfit Oy, Oulu (FI); Metso Paper, Inc, Helsinki (FI)

( * ) Notice: Subject to any disclaimer, the term of this patent is extended or adjusted under 35 U.S.C. 154(b) by 781 days.

(21) Appl. No.: 11/912,968

(22) PCT Filed: May 15, 2006

(86) PCT No.: PCT/FI2006/050192
§ 371 (c)(1),
(2), (4) Date: Oct. 29, 2007

(87) PCT Pub. No.: WO2006/123017
PCT Pub. Date: Nov. 23, 2006

(65) Prior Publication Data
US 2008/0211516 A1  Sep. 4, 2008

(30) Foreign Application Priority Data
May 17, 2005  (FI) ..................................... 20055231

(51) Int. Cl.
*G01R 27/04* (2006.01)
*G01N 5/02* (2006.01)
(52) U.S. Cl. .......................................... 324/634; 73/73
(58) Field of Classification Search .................. 324/634, 324/633
See application file for complete search history.

(56) References Cited

U.S. PATENT DOCUMENTS

| | | | |
|---|---|---|---|
| 3,829,764 A | 8/1974 | Bosisio | |
| 4,155,035 A | 5/1979 | Fitzky | |
| 4,504,788 A * | 3/1985 | Froncisz et al. | 324/316 |
| 5,315,258 A | 5/1994 | Jakkula et al. | |
| 5,349,845 A | 9/1994 | Blom | |
| 5,826,458 A | 10/1998 | Little | |
| 5,859,536 A * | 1/1999 | Stockton | 324/664 |
| 6,111,415 A * | 8/2000 | Moshe | 324/640 |
| 6,476,619 B1 * | 11/2002 | Moshe et al. | 324/634 |
| 6,837,122 B2 * | 1/2005 | Herrmann et al. | 73/865 |
| 6,897,659 B2 * | 5/2005 | Herrmann et al. | 324/633 |
| 7,982,469 B2 * | 7/2011 | Jakkula et al. | 324/633 |
| 2006/0028213 A1 | 2/2006 | Typpo et al. | |

FOREIGN PATENT DOCUMENTS

| | | |
|---|---|---|
| DE | 19741519 1 A | 3/1999 |
| EP | 0845754 | 6/1998 |
| EP | 0903657 B1 | 4/2002 |
| EP | 1331476 A1 | 7/2003 |
| GB | 1470592 | 4/1977 |
| GB | 2260408 | 4/1993 |
| JP | 56039477 | 4/1981 |
| WO | WO /2005 012887 | 2/2005 |

OTHER PUBLICATIONS

Office Action for corresponding Finnish priority application No. 20055231; issued Nov. 11, 2006.

* cited by examiner

*Primary Examiner* — Jeff Natalini
(74) *Attorney, Agent, or Firm* — Hoffmann & Baron LLP

(57) ABSTRACT

For measuring the water content of a web in the wire section of a paper machine, at least one radiofrequency-operated resonator sensor forms an electric near field, in which a web affects the resonance frequency of each resonator sensor. The water content of the web is measured as a function of the resonance frequency of each resonator sensor in a measuring unit.

17 Claims, 4 Drawing Sheets

METHOD AND MEASURING INSTRUMENT FOR MEASURING WATER CONTENT

CROSS-REFERENCE TO RELATED APPLICATIONS

This application is a National Phase application of International Application No. PCT/FI2006/050192 filed May 15, 2006, which claims priority based on Finnish Patent Application No. 20055231, filed May 17, 2005, which are incorporated herein by reference.

BACKGROUND OF THE INVENTION

1. Field of the Invention

The invention relates to a method and measuring instrument for measuring the water content of a web in the wire section of a paper machine.

2. Description of the Related Art

Accurate measuring of the water content of a paper web makes it possible to accurately adjust the paper machine and to make good quality paper. If the adjustment fails, the paper web becomes uneven in its properties and poor in quality. In the wire section in particular, it is possible to measure the amount of drained water as a machine direction (MD) function.

Water content is often measured by means of gamma radiation. In this measurement, the radiation source emits gamma radiation to the web, from which it scatters back to a detector or proceeds through the web to a detector. The density of the wire, the density of fibres and fillers and the like used in papermaking and the density of water affect the measuring result. Because the amount of water decreases as the web moves in the wire section, the effect of the water density on the measuring result diminishes accordingly. Thus, a change in the measuring result shows a change in the amount of water, i.e. water drainage in the wire section in machine direction.

However, this solution involves problems. Gamma radiation is ionising radiation, which is harmful to the people close to the measuring instrument. In addition, the area of influence of the radiation is so wide that using gamma radiation in close quarters is not sensible. Also, moving a gamma source from one place or country to another is difficult due to safety regulations, because a gamma source cannot be switched off.

Ultrasound technique has also been used in measuring water amounts and drainage. However, ultrasound measurement is not very accurate especially at low water contents, and air in the web also disturbs the measurement very much.

SUMMARY OF THE INVENTION

It is an object of the invention to provide an improved method and a measuring instrument implementing the method. This is achieved by a method for measuring the water content of a web in the wire section of a paper machine. The method comprises forming with at least one radiofrequency-operated resonator sensor an electric near field, in which a web affects the resonance frequency of each resonator sensor, and measuring the water content of the web as a function of the resonance frequency of each resonator sensor.

The invention also relates to a measuring instrument for measuring the water content of a web in the wire section of a paper machine. The measuring instrument comprises at least one electrically operated and high-frequency resonator sensor and a measuring unit, and during measuring, each of the resonator sensors is arranged to form an electric near field, in which during measuring the object to be measured affects the resonance frequency of each resonator sensor, and the measuring unit is arranged to measure the water content of the object to be measured as a function of the resonance frequency of at least one resonator sensor.

Preferred embodiments of the invention are disclosed in the dependent claims.

The methods and measuring instrument of the invention provide several advantages. The measuring instrument is accurate, and does not have any problems with safety. The radiation of the measuring instrument is also simple to control.

BRIEF DESCRIPTION OF THE DRAWINGS

The invention will now be described in greater detail by means of preferred embodiments and with reference to the attached drawings, in which.

DETAILED DESCRIPTION OF THE PREFERRED EMBODIMENTS

When equations representing a high-frequency electric field are formed on a dipole or emitter, it is observed that, up close, the high powers of the distance and, far away, the low powers of the distance determine the value of the field expression. The matter can be illustrated by an example equation that in general represents the electric field E of the emitter as a function of the distance:

$$E = \sum_{i=1}^{M} A_i (kR)^{-i}, \qquad (1)$$

wherein i is an index, M is the highest required power, $A_i$ is a required coefficient, k is a wave number, $k=2\pi/\lambda$, wherein $\lambda$ is the radiation wavelength and $\pi$ is constant, $\pi \approx 3,1415926$, and R is the distance from the emitter. When the distance R is small, i.e. this is a near field (kR<1), the sum expression is governed by the term $(kR)^{-M}$, and the value of the power M is then often 2 or 3. When the distance R is great, i.e. this is a far field (kR>1), the sum expression is governed by the term $(kR)^{-1}$. An electric near field thus resembles the field of a static dipole. A boundary B between a far field and a near field can also be defined even more accurately than above by means of a dimension D (such as the diameter of an antenna) of an emitter aperture and wavelength $\lambda$ as follows:

$$B=(2D^2)/\lambda. \quad (2)$$

In such a case, an electric field whose distance from the emitter is the same or shorter than B is in the near field. Correspondingly, an electric field whose distance from the emitter is longer than B is in the far field.

In the presented solution, one object is that the emitter, or rather resonator, acting as a sensor not radiate, at least not very much, in the far field, and the electric field in its entirety or for a major part outside the resonator structure is a near field. The far field can be restricted by means of the structure of the resonator sensor. This way the resonator sensor does not disturb other devices or resonator sensors.

Figure 1A:
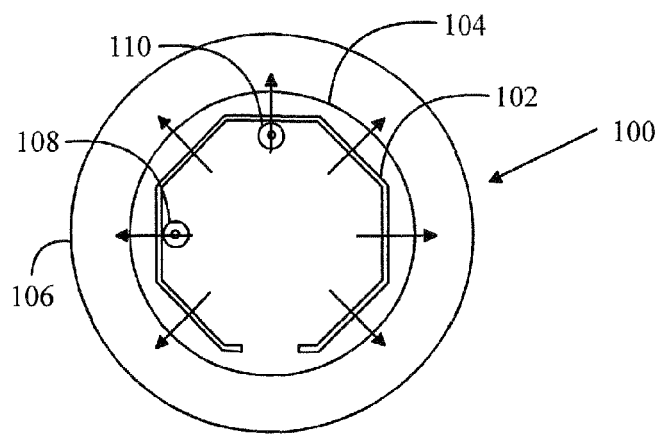
FIG. 1A is a top view of a slotted resonator sensor.
Figure 1B:
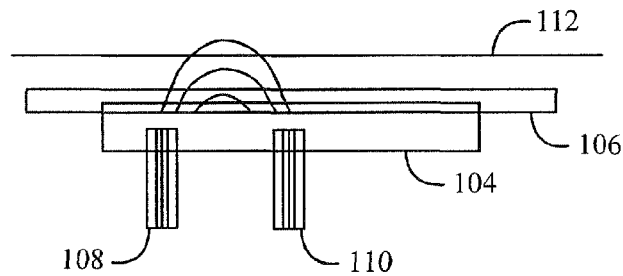
FIG. 1B is a side view of a slotted resonator sensor.

With reference to FIGS. 1A and 1B, let us now examine the structure of a resonator sensor. FIG. 1A is a top view of a resonator sensor and FIG. 1B shows a resonator sensor from the side. The resonator sensor 100 may comprise a radiating slot 102 in a metal plate 104, which may be the metal coating of a circuit board, for instance. The curved slot 102 may form (nearly) a circle, in which case the electric field it radiates to a far field is (nearly) entirely cancelled out. The centreline of the slot 102 may also form a curve that is piece-wise linear. The centreline of the slot 102 may also form a curve that curves continuously, for instance with a non-linear function with a continuous derivate. The centreline of the slot also represents a curved non-self-intersecting curve. The sum of the electric field vectors drawn in the figure with an arrow is thus (nearly) zero. In FIGS. 1A and 1B, only the upward-oriented electric field vector does not have an opposite vector and, therefore, the resonator sensor radiates to some extent. On the metal plate 104, there may be an electrically insulated layer 106, which may be of glass. An input and receiving port 108, 110 for radio frequency signals may be located as desired. The water layer 112 to be measured is on the sensor 100 during measuring. The field lines of the electric near field can be drawn to start from the resonator sensor and to curve toward the edges of the slot. The field lines run through the water layer 112.

Figure 2A:
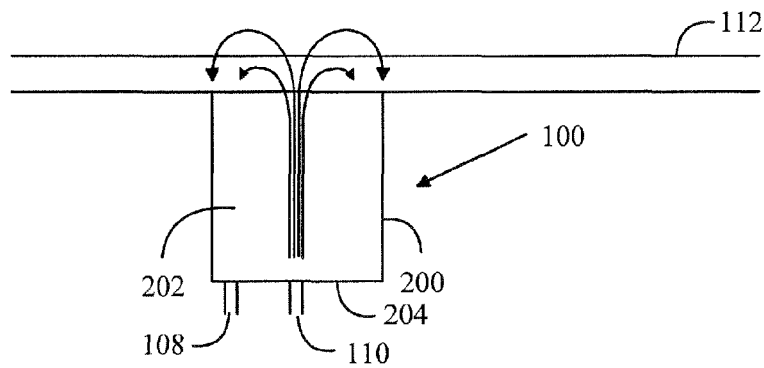
FIG. 2A is a side view of a resonator sensor based on a round waveguide.
Figure 2B:
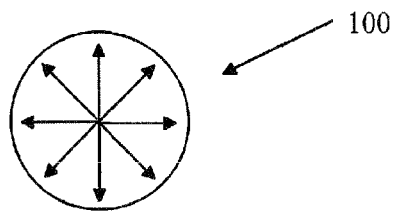
FIG. 2B is a top view of a resonator sensor based on a round waveguide.

FIGS. 2A and 2B show a different resonator sensor 100 with a waveguide that may be round or angular. The outer shell 200 of the resonator sensor that produces a short circuit in the bottom section may be of metal or some other electrically conductive material, and there may be an electrically insulating material 202, such as plastic or ceramic, inside the outer shell. The water layer 112 to be measured is on the sensor 100 during measuring. The field lines of the electric near field can then be drawn to start from the centre of the resonator sensor and to curve toward the outer shell 200. A resonator sensor 100 of this type never forms a far field and, thus, does not emit electromagnetic radiation. A resonator sensor having a round cross-section may operate on a non-radiating waveform $TM_{01}$, and a resonator sensor having a rectangular or square cross-section may operate on a non-radiating waveform $TM_{11}$. The bottom 204 of the resonator sensor 100 may be made of an electrically conductive material that may be the same material as in the rest of the outer shell 200.

FIG. 2B shows the field lines of an electric near field from the top. The input and receiving port 108, 110 for radio frequency signals may be located in the centre and edge of the resonator sensor as shown in FIGS. 2A and 2B.

Figure 2C:
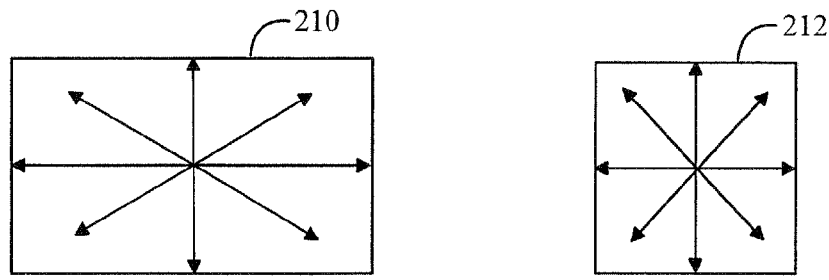
FIG. 2C is a top view of a resonator sensor based on an angular waveguide.

FIG. 2C shows a rectangular resonator sensor 210 and a square resonator sensor 212. As can be seen in the Figure, there is an opposite vector for each field vector representing the electric field, which is why there is no far field.

Figure 3A:
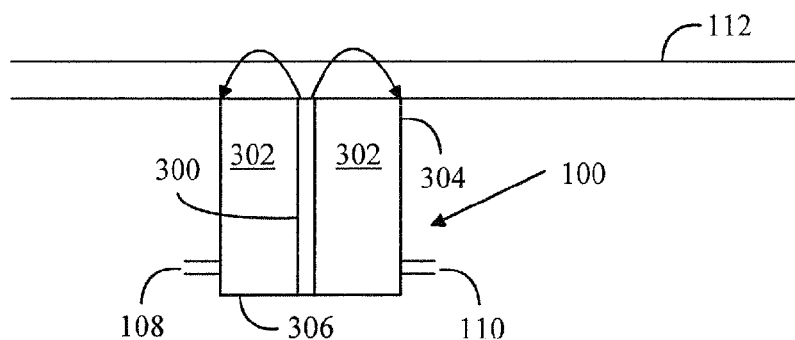
FIG. 3A is a side view of a coaxial resonator.
Figure 3B:
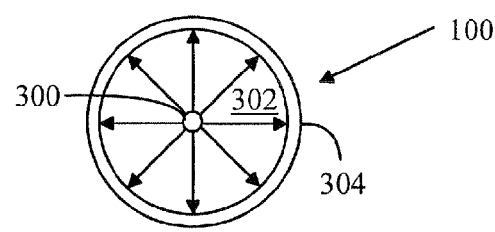
FIG. 3B is a top view of a coaxial resonator.

FIGS. 3A and 3B show yet another possible resonator sensor 100 that is a coaxial resonator. In this solution, there is metal or some other electrically conductive material 300 at the centre of the resonator sensor. Around the electrically conductive centre part 300, there is an insulating material 302, such as plastic or ceramic. The outer rim 304 of the coaxial resonator is, in turn, made of an electrically conductive material in the same manner as the centre part 300. The bottom section of the coaxial resonator is short-circuited with an electrically conductive material 306 that may be the same material as in the centre part 300 and the outer rim 304. In this solution, too, the field lines of the electric near field can be drawn to start from the centre of the resonator sensor and to curve toward the edges. A resonator sensor 100 of this type does not form a far field and, thus, does not emit electromagnetic radiation.

FIG. 3B shows the field lines of an electric near field from the top.

Figure 4:
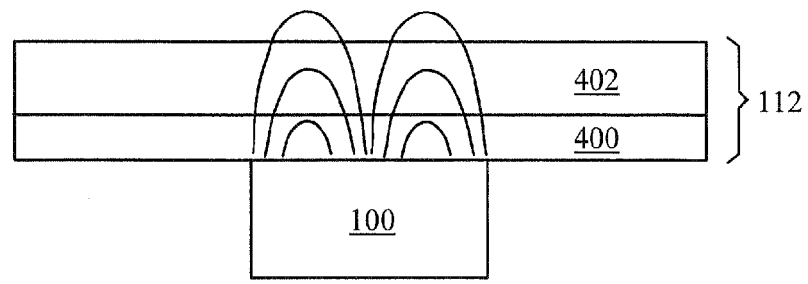
FIG. 4 shows the operation of a resonator sensor.

FIG. 4 shows the operation of a resonator sensor 100. In this example, the water layer to be measured is contained in both the wire 400 and the web 402. The electric near field from the resonator sensor extends through both the wire 400 and the web 402 on the used wavelength, because the measuring is done in the near field in which the distance between the resonance sensor 100 and the web 402 is shorter than the wavelength of the resonance frequency. Thus, the electric near field interacts with the wire 400, web 402, and the water in them, and this is why the resonance frequency of the resonator sensor 100 depends on the wire 400, web 402, and amount of water, of which only the amount of water varies. The resonator sensor does not sweep-search for the resonance frequency, but the resonator sensor automatically finds and locks onto the resonance frequency due to its properties that are influenced by the wire, web, and amount of water, among other things. The resonator sensor can, thus, be thought to be based on a self-oscillating oscillator that locks onto a resonance.

Figure 5:
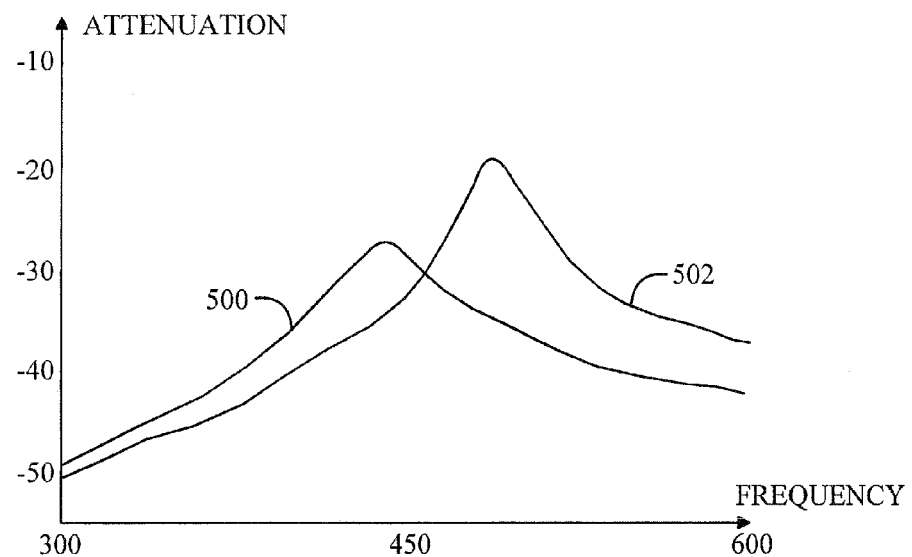
FIG. 5 shows the measurement of resonance frequencies with and without water.

FIG. 5 shows two different measurements of the resonance frequency as a function of the amount of water. The vertical axis shows the attenuation of the resonance sensor on a decibel scale, and the horizontal axis shows the radio frequency from 300 to 600 MHz. Curve 500 shows a situation in which the layer on top of the resonator sensor is 5 mm thick (or corresponding to this), and curve 502 shows a situation in which there is no water. The maximum values of the curves refer to resonance frequencies, which for water is approximately 440 MHz and without water 490 MHz in this figure.

Figure 6:
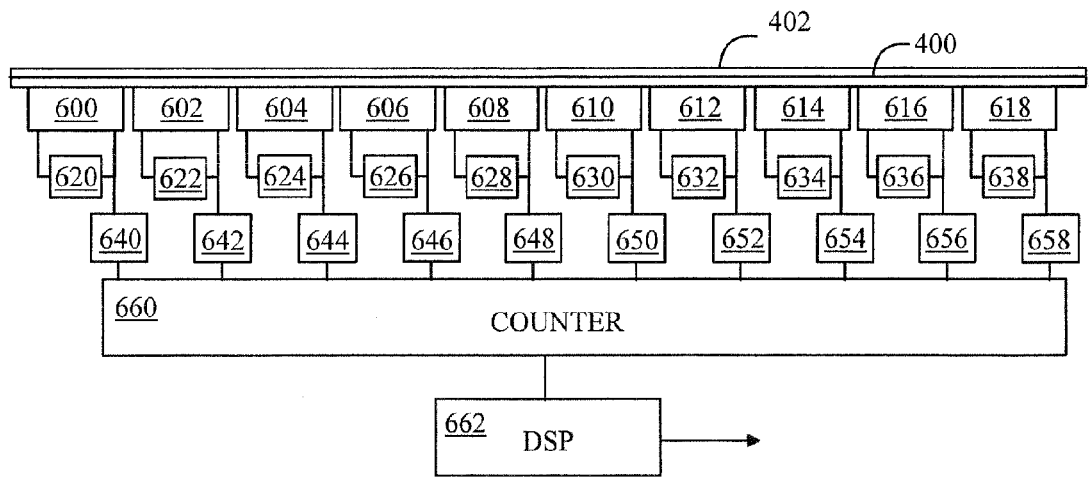
FIG. 6 shows the positioning of a line of resonator sensors beneath a wire.

FIG. 6 shows a solution in which a line of resonator sensors is positioned below the web in cross direction (CD). The resonance frequency of the resonator sensors 600 to 618 in the line depends on the amount of water bound to the wire 400 and web 402 on top of them. Amplifiers 620 to 638 supply the electric power required for the resonance to the resonator sensors and amplify the resonance frequency signals that can be transmitted by directional couplers (not shown in the figure), for instance, to dividers 640 to 658. Each combination of an amplifier and resonator sensor forms an oscillator that oscillates on a specific frequency depending on the amount of water. The dividers 640 to 658 divide the signal frequencies into smaller ones. The dividers 640 to 658 may operate such that when dividing the frequency by N, which is a real number higher than one, each divider transmits one pulse N times less frequently with respect to the resonance frequency $f_r$. N is often an integer. A counter 660 may count the number of pulses received at the counter 660 within a predefined time $\Delta t$. The frequency $f_p$ of the pulses is then $f_r/N$, wherein $f_r$ is the resonance frequency. The number of pulses PM in one resonator sensor within a predefined time Δt is PM=Δt·$f_p$. The predefined time Δt can be adjusted to the frequency division, i.e. to N, so as to receive a suitable number of pulses to the counter within the predefined time. When dividing the resonance frequency $f_r$ with such a number N that the pulses arrive on a frequency $f_p$ of tens or hundreds of kilohertz, the predefined time Δt of the counter may be milliseconds or tens of milliseconds, for instance. The resonance frequency of the resonator sensor may be 100 MHz to 100 GHz, for instance. N may then be 10,000 to 10,000,000. When the counter 660 has established the number of pulses, the information is transmitted to a measuring unit 662 that is a digital signal-processing device, for instance. The measuring unit 662 can determine the water content, because the number of pulses PM is proportional to the resonance frequency that, in turn, is proportional to the amount of water. All the resonance sensors in the line may perform the measurement simultaneously, i.e. the movement of the wire or a change in the movement does not affect the measurement and, therefore, crosswise measuring can be done at right-angles across the web. When the counter 660 has calculated the number of current pulses, it can start a new measurement and, this way, it is possible to perform consecutive and continuous measurement of the water amount. The counter 660 may be implemented by using FPGA (Field Programmable Gate Array), EPLD (Electrically Programmable Logic Device), or CPLD (Complex Programmable Gate Array) circuits, for instance.

It is also possible to enter into the measuring unit 662 reference values that correspond to measuring just the wire at the same points where the common water content of the web and wire was measured. This way, the measuring unit 662 can remove the impact of the wire from the measurements, in which case for instance the impact of water in the wire can be eliminated.

Figure 7:
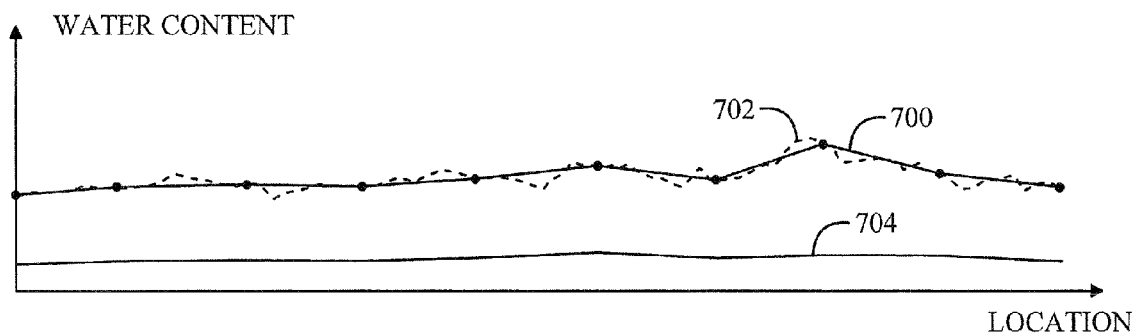
FIG. 7 shows a transverse water amount measurement of a web.

FIG. 7 shows a transverse water-content measurement of a web. The vertical axis shows the water content on a freely selected scale, and the horizontal axis shows the location in cross-direction. Points 700 that are marked by dots and joined by a uniform line correspond to the results measured by the ten resonator sensors of FIG. 6. Dashed line 702 shows a more accurate measurement of the point. The tendency in the measurement according to this example is that the amount of water increases toward the right until the reference numbers and begins to decrease after them.

Figure 8:
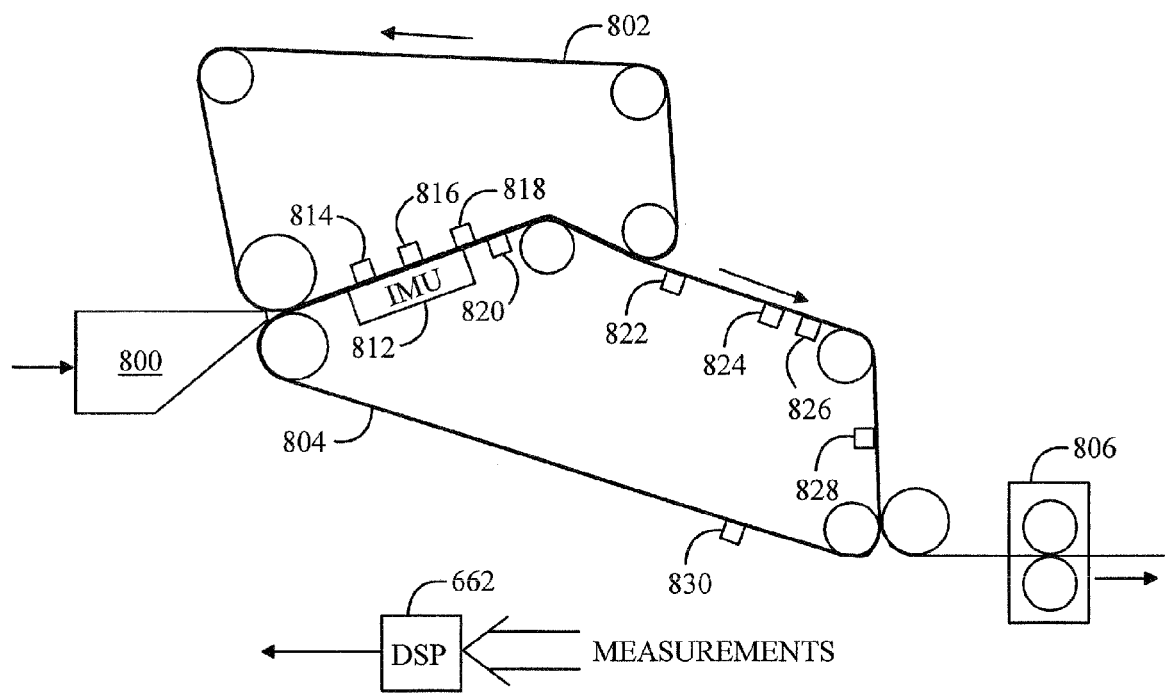
FIG. 8 shows a measuring arrangement on a paper machine.

FIG. 8 shows a measuring arrangement in a paper machine. This section of the paper machine usually comprises a headbox 800, top wire 802, bottom wire 804, and press part 806. In the wire section, which comprises the above-mentioned parts excluding the headbox 800 and press part 806, a web running on top of the bottom wire 804 can be dewatered by means of vacuum-operated suction boxes 812, for instance. In addition or alternatively, at least some of the rolls are usually suction rolls for dewatering the web. If several resonator sensors are used, water content can be measured with resonator sensors 814 to 828 at different points of the wire. Consecutive measurements help define the decrease in water content as the web moves on along the wire section. If water drainage is to be accurately determined in the longitudinal direction of a web, the measurements at different points of the wire section should be synchronized with the movement of the web. The web is then measured accurately in consecutive measurements at different points of the wire section, and it is possible to determine water drainage from the wire section on the basis of the differences of the water content measured at corresponding points of the web. If the measuring is done using several resonator sensors in the cross-direction of the wire, it is possible to determine the water drainage distribution provided by the wire section in the cross-direction of the web on the basis of the differences in the water contents measured at the corresponding points of the web. Such a measuring result corresponds to the difference of curves 700 and 704 in FIG. 7.

With one line of resonator sensors, the measuring can for instance be done using a resonator sensor line 828 at the end of the wire section. The water content of just the wire can for instance be determined with a resonator sensor line 830, and this measurement can be used as reference when deleting the impact of the wire's water content from the joint water content measurement of the wire and web. The average water content of the wire can also be estimated or measured separately in a laboratory in advance, after which the water content of the web can be determined without any separate reference measurement made with one or more resonator sensors.

Figure 9:
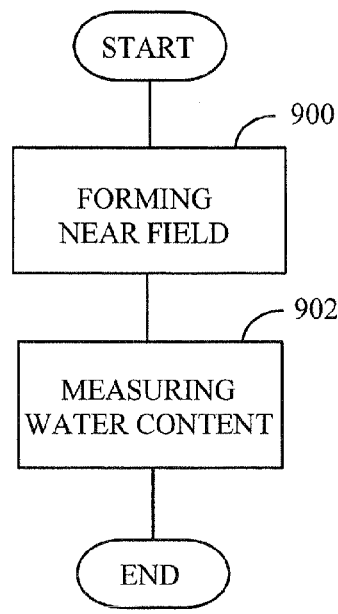
FIG. 9 is a flow chart of a water amount measuring method.

FIG. 9 further shows a flow chart of a water content measurement method. In step 900, at least one radiofrequency-operated resonator sensor forms an electric near field, and a web in the field affects the resonance frequency of the resonator sensor. In step 902, the water content of the web is measured as a function of the resonance frequency of each resonator sensor.

Many of the steps (such as 902) in the methods can be executed with a computer program, for instance, which contains routines for the execution of the method steps. Instead of a computer program, the measuring unit 662 can use a hardware solution, such as one or more application-specific integrated circuits (ASIC) or as a functional logic constructed of separate components.

Even though the invention is described above with reference to the examples shown in the attached drawings, it is clear that the invention is not restricted to them but can be modified in many ways within the scope of the attached claims.

What is claimed is:

1. A method for measuring the water content of a web in the wire section of a paper machine, the method comprising
    forming only an electric near field of a transverse magnetic waveform with at least two radiofrequency-operated resonator sensors arranged in a line, in which a web affects the resonance frequency of each resonator sensor; and
    measuring the water content of the web as a function of the resonance frequency of the electric near field of at least two resonator sensors simultaneously.

2. A method as claimed in claim 1, the method further comprising using a resonator sensor whose structure limits an electric far field propagating as radiation and extending outside the resonator sensor.

3. A method as claimed in claim 1, the method further comprising measuring the water content of the web in cross-direction by means of several resonator sensors.

4. A method as claimed in claim 1, the method further comprising measuring in a synchronized manner the water content of the web at least at two different points of the wire section in such a manner that the measurements are directed to the same point of the web; and
    determining water drainage from the wire section on the basis of the differences in water contents measured at corresponding points of the web.

5. A method as claimed in claim 1, the method further comprising measuring in a synchronized manner the water content of the web at least at two different points of the wire section in the cross-direction of the web by using several resonator sensors in such a manner that the measurements are directed to the same points of the web; and determining the water drainage distribution provided by the wire section in the cross-direction of the web on the basis of the differences in the water contents measured at the corresponding points of the web.

6. A method as claimed in claim 1, the method further comprising:
measuring a water content reference value for each resonator sensor by measuring a water content of the wire only;
measuring a joint water content of the web and wire; and
determining the water content of the web by deducting the water content of the wire only from the joint water content of the web and wire.

7. A method as claimed in claim 1, the method further comprising measuring the water content of the web with a slotted resonator, in which the centerline of the slot represents a curved non-self-intersecting curve.

8. A method as claimed in claim 1, the method further comprising measuring the water content of the web with a waveguide resonator that uses a non-radiating waveform.

9. A method as claimed in claim 1, the method further comprising measuring the water content of the web with a coaxial resonator.

10. A measuring instrument for measuring the water content of a web in the wire section of a paper machine, wherein the measuring instrument comprises:
at least two electrically operated and high-frequency resonator sensors arranged in a line; and a measuring unit, during measuring each of the resonator sensors is arranged to form only an electric near field of a transverse magnetic waveform, in which during measuring the object to be measured affects the resonance frequency of each resonator sensor, and
the measuring unit is arranged to measure the water content of the object to be measured as a function of the resonance frequency of the electric near field of at least two resonator sensors simultaneously.

11. A measuring instrument as claimed in claim 10, wherein each of the resonator sensors is arranged to limit an electric far field propagating as radiation and extending outside the resonator sensor.

12. A measuring instrument as claimed in claim 10, wherein the measuring instrument comprises at least two resonator sensors for measuring in a synchronized manner the water content of the web at least at two points of the wire section in such a manner that the measurements are directed to the same point of the web; and
the measuring unit is arranged to determine water drainage from the wire section on the basis of the differences in water contents measured at corresponding points of the web.

13. A measuring instrument as claimed in claim 10, wherein the measuring instrument comprises at least two lines of resonator sensors in the cross-direction of the web, each line comprising at least two resonator sensors, for measuring in a synchronized manner the water content of the web at least at two different points of the wire section in the cross-direction of the web in such a manner that the measurements are directed to the same points of the web; and
the measuring unit is arranged to determine the water drainage distribution provided by the wire section in the cross-direction of the web on the basis of the differences in the water contents measured at the corresponding points of the web.

14. A measuring instrument as claimed in claim 10, wherein the measuring instrument comprises at least one resonator sensor for measuring a water content of the wire only, the measuring unit being arranged to measure a joint water content of the web and wire, and determine the water content of the web by deducting the water content of the wire only from the joint water content of the web and wire.

15. A measuring instrument as claimed in claim 10, wherein at least one of the resonator sensors is a slotted resonator, in which the centreline of the slot represents a curved non-self-intersecting curve.

16. A measuring instrument as claimed in claim 10, wherein at least one of the resonator sensors is a waveguide resonator that is arranged to use a non-radiating waveform.

17. A measuring instrument as claimed in claim 10, wherein at least one of the resonator sensors is a coaxial resonator.

* * * * *